United States Patent
Cahill

(10) Patent No.: US 9,498,613 B2
(45) Date of Patent: Nov. 22, 2016

(54) ROTARY TATTOO MACHINE WITH SUSPENDED MOTOR GIVE

(71) Applicant: Richard M. Cahill, Frenchtown, NJ (US)

(72) Inventor: Richard M. Cahill, Frenchtown, NJ (US)

(*) Notice: Subject to any disclaimer, the term of this patent is extended or adjusted under 35 U.S.C. 154(b) by 371 days.

(21) Appl. No.: 14/120,802

(22) Filed: Jul. 1, 2014

(65) Prior Publication Data
US 2016/0001054 A1 Jan. 7, 2016

(51) Int. Cl.
*A61M 37/00* (2006.01)

(52) U.S. Cl.
CPC .................. *A61M 37/0076* (2013.01)

(58) Field of Classification Search
CPC ............. A61M 37/0076; A61M 2005/31588; A61M 2202/0468; A61M 2205/10; A61M 2205/33; A61M 35/006; A61M 5/31546; A01K 11/005
See application file for complete search history.

(56) References Cited

U.S. PATENT DOCUMENTS

| | | | |
|---|---|---|---|
| 4,204,438 A | 5/1980 | Binaris et al. | |
| 5,551,319 A | 9/1996 | Spaulding et al. | |
| 6,033,421 A | 3/2000 | Theiss et al. | |
| 6,282,987 B1 | 9/2001 | Moniz | |
| 7,748,294 B2* | 7/2010 | Jarboe | A61M 37/0076 30/362 |
| 7,908,943 B2 | 3/2011 | Beyer | |
| 8,236,021 B2 | 8/2012 | Kluge et al. | |
| 8,518,071 B2 | 8/2013 | Kluge | |
| 8,733,211 B2* | 5/2014 | Snijders | A61M 37/0076 30/362 |

* cited by examiner

*Primary Examiner* — Robert Scruggs
(74) *Attorney, Agent, or Firm* — Kenneth P. Glynn; Deirdra M. Meagher

(57) ABSTRACT

A rotary tattoo machine with suspended motor give, includes: a frame adapted to receive and support rotary tattoo machine components; a spring mechanism having at least one spring connected to the frame; a D.C. rotary drive motor connected to the at least one spring and rotatably suspended from the spring mechanism relative to the frame, the D.C. rotary drive motor having a drive shaft and a cam extending therefrom; a needle drive mechanism connected to the cam; and, a tattoo needle connected to the needle drive mechanism. There is an optional spring tension adjustment mechanism connected to the at least one spring.

20 Claims, 4 Drawing Sheets

ROTARY TATTOO MACHINE WITH SUSPENDED MOTOR GIVE

REFERENCE TO RELATED APPLICATIONS

The present application is not related to any pending or issued United States of America or foreign patent or patent application.

BACKGROUND OF INVENTION a. Field of Invention

The present invention generally relates to tattoo machines of the rotary type, and more specifically such rotary tattoo machines that both have give and are excellent for both line aspects of tattoos and for shading aspects of tattoos. The machines have D.C. motors that are suspended from their frames via a spring mechanism, e.g., one or more springs or one or more springs with rotation lever(s).

b. Description of Related Art

The following patents are representative of the field pertaining to the present invention:

U.S. Pat. No. 8,733,211 B2 to Snijders describes tattoo machines include a motor pivotably coupled to a frame. The motor includes an eccentrically weighted shaft. A needle drive mechanism is coupled with the motor. Methods of making tattoo machines may include obtaining a frame and obtaining a motor that includes an eccentrically weighted shaft. The motor can then be coupled to the frame so that the motor is able to pivot about a pivot axis. Methods operational for tattoo machines include rotating an eccentrically weighted shaft on a motor that is pivotably coupled to a frame. The motor is pivoted about a pivot axis as a result of the rotation of the shaft.

U.S. Pat. No. 8,518,071 B2 to Kluge describes a driving device for a device for the local puncturing of a skin, particularly for the application of permanent make-up or a tattoo, as well as a method for operating the driving device. The driving device comprises a drive mechanism for producing a repetitive thrust movement at a frequency, which is usable for the retraction/extension of a puncturing mechanism, a detection apparatus with which a parameter is detectable, which indicates a resistance force acting against the repetitive thrust movement, a setting apparatus with which, for the case that a changed resistance force is detected with the detection apparatus, can be pre-set by a user into an operating mode of increased frequency in which the frequency is increased after detection of the changed resistance force, or an operating mode of reduced frequency in which the frequency is reduced after detection of the changed resistance force, and a control apparatus coupled to the detection apparatus and the setting apparatus, the control apparatus automatically causes the frequency change of the increased frequency mode and the reduced frequency mode.

U.S. Pat. No. 8,236,021 B2 to Kluge et al. describes a handheld device for the repetitive local puncturing of a skin for an input of a liquid active substance, particularly a permanent make-up and tattoo handheld device, with: a piercing device formed in a needle module with repetitive movement forwards and backwards, which piercing device is driven with the help of a drive unit formed in a drive module, a reservoir for the liquid active substance, a pump system coupled to the reservoir where the said pump system is configured in order to discharge the liquid active substance held in a cavity of the reservoir by means of pressure application, and a fluid connection running at least partially in a needle module casing where said fluid connection is configured in order to supply the liquid active substance from the reservoir to the piercing device.

U.S. Pat. No. 7,908,943 B2 to Beyer describes through putting the coils of a tattoo machine in an angle and mounting an equivalently bent hammer on an angle fixed spring mount we obtain a machine that is stronger than other machines compared in size and lighter and shorter than other machines that are comparable in power. A marking device with an oscillating needle. The needle is attached through a needle bar on an armature bar which is attracted by an electromagnetic assembly. A from rear to front ascending angled stair-like milled yoke supports the electromagnetic assembly, which consists of one lower and one higher coil. A spring mount with an adequate angle is mounted to the side plates. An inversely proportional bent armature bar levels that before mentioned angle. The armature bar is attached through a spring to the spring mount. The angle of the set-up procures the oscillating armature bar with both forth and downward motion, following a so called arc principle. The air gap between the front coil and the armature bar is effectively smaller. The needle hits the skin not in a straight motion but in a diving motion. Thus, the resistance of the skin is easier to overcome.

U.S. Pat. No. 6,282,987 B1 to Moniz describes a contact bar assembly for a tattooing device having a spring saddle frame comprising an arcuate contact arm supporting a contact screw for making electrical contact with the contact spring. The proximate end of the contact arm is slotted for adjustment in a longitudinal direction. The distal end of the contact arm has a cylindrical lug disposed horizontally adapted to receive a cylindrical rod insert having a threaded axial bore. The lug has a pair of opposed slots for reception of the threaded contact screw, which also threads through the rod insert enabling adjustment of the contact screw in vertical or angular movement in the lug. The contact bar assembly is lightweight, balanced, and adjustment thereof is possible with the opposite free hand by either a right or left-handed tattooist.

U.S. Pat. No. 6,033,421 to Theiss et al. describes a handheld tattoo machine with a low vibration drive unit and an offset, removable driven grip tube. The drive unit includes a rotatable drive shaft; a cam attached to the distal end of the shaft, the cam having a cam face at an angle to the longitudinal axis of the drive shaft; and a drive housing enclosing the drive shaft and cam. The drive housing includes a driven grip tube receiving bore having a longitudinal axis parallel to and offset from the longitudinal axis of the drive housing to facilitate ease of use by the operator. The removable driven grip tube includes a reciprocal needle bar having a cam follower at a proximal end and a needle attachment surface at a distal end.

U.S. Pat. No. 5,551,319 to Spaulding et al. describes a marking device with a reciprocating needle. The needle is attached to an armature which reciprocates in a slot in housing by a crank which is rotated by a motor in the housing. Vibration of the motor and tolerances between the armature and track cause unwanted movements of the needle in a plane perpendicular to the reciprocating motion. Guide bars and bushings connect the armature to the track. Tolerances between the guide bars and bushings are less than tolerances between the armature and track. An armature bracket is detachably connected to the housing in order to partially or fully close off an open end of the track after the armature has been inserted into the track. Guide bars and bushings then connect the armature and the armature bracket. The motor is supported on only one end by bolts extending from a mounting wall inside the housing. A damping plate is positioned between the motor and the mounting wall, and a damping ring is positioned between, and contacts, the damping ring and the housing. The damping ring is made of material to absorb or block vibrations. Undesirable movements due to a vibration of the motor and tolerances between the armature and the housing are thus removed.

U.S. Pat. No. 4,204,438 to Binaris et al. describes a tattooing device which includes a motor housing and a needle housing secured thereto. A motor and an eccentric drive structure driven by the motor are mounted in the motor housing. In addition, a needle shaft and tattooing needle are mounted for reciprocation in the needle housing and are driven to reciprocate by the eccentric drive structure in the motor housing. The needle housing has an opening at the lower end thereof through which the tattooing needle reciprocates, and a silicone rubber bushing is mounted in the needle housing and is provided with an opening through which the needle extends. The diameter of the bushing opening is less than the diameter of the opening in the lower end of the needle housing so that the bushing operates to constrain transverse movement of the reciprocating needle and thereby reduces noise, ink splatter, the tearing of skin, and improves line clarity. In a preferred embodiment, the motor housing is provided with a mercury switch for energizing and de-energizing the motor so that the tattooing device can be operated with only one hand.

Notwithstanding the prior art, the present invention is neither taught nor rendered obvious thereby.

SUMMARY OF INVENTION

The present invention is a rotary tattoo machine with suspended motor give, which comprises: a) a frame adapted to receive and support rotary tattoo machine components; b) a spring mechanism having at least one spring connected to the frame; c) a D.C. rotary drive motor connected to the at least one spring and rotatably suspended from the spring mechanism relative to the frame, the D.C. rotary drive motor having a drive shaft and a cam extending therefrom; d) a needle drive mechanism connected to the cam; and, e) a tattoo needle connected to the needle drive mechanism.

In some preferred embodiments of the present invention rotary tattoo machine, the D.C. rotary drive motor includes connection for a power unit having a corresponding complementary connection of a transformer with a power source connection.

In some preferred embodiments of the present invention rotary tattoo machine, the machine further includes the transformer connected thereto. In some preferred embodiments of this present invention rotary tattoo machine, the transformer is a variable power adjustable transformer.

In some preferred embodiments of the present invention rotary tattoo machine, the spring mechanism is at least one spring extending from the frame to the D.C. rotary.

In some preferred embodiments of the present invention rotary tattoo machine, the spring mechanism is a rotatable lever connected to the frame and to the D.C. rotary drive motor and at least one spring connected to the lever and the frame.

In some preferred embodiments of the present invention rotary tattoo machine, the spring is selected from the group consisting of a leaf spring, a coil spring and a bar spring. In some preferred embodiments of this present invention rotary tattoo machine, the spring is a spring made of a material selected from the group consisting of metal, plastic and combinations thereof.

In some preferred embodiments of the present invention rotary tattoo machine, the spring mechanism includes an attachment component that is connected to and removable from the frame.

In some preferred embodiments of the present invention rotary tattoo machine, the at least one spring is a single spring.

In some preferred embodiments of the present invention rotary tattoo machine, there is also an adjustment capability to change spring tension to adapt to various types of recipients. Thus, in these embodiments of the present invention rotary tattoo machine, there are: a) a frame adapted to receive and support rotary tattoo machine components; b) a spring mechanism having at least one spring connected to the frame; c) a spring tension adjustment mechanism connected to the at least one spring; d) a D.C. rotary drive motor connected to the at least one spring and rotatably suspended from the spring mechanism relative to the frame, the D.C. rotary drive motor having a drive shaft and a cam extending therefrom; e) a needle drive mechanism connected to the cam; and, f) a tattoo needle connected to the needle drive mechanism.

In some preferred embodiments of the present invention rotary tattoo machine having a spring tension adjustment feature, the D.C. rotary drive motor includes connection for a power unit having a corresponding complementary connection of a transformer with a power source connection.

In some preferred embodiments of the present invention rotary tattoo machine having a spring tension adjustment feature, the machine further includes the transformer connected thereto. In some preferred embodiments of the present invention rotary tattoo machine having a spring tension adjustment feature, the transformer is a variable power adjustable transformer.

In some preferred embodiments of the present invention rotary tattoo machine having a spring tension adjustment feature, the spring mechanism is at least one spring extending from the frame to the D.C. rotary.

In some preferred embodiments of the present invention rotary tattoo machine having a spring tension adjustment feature, the spring mechanism is a rotatable lever connected to the frame and to the D.C. rotary drive motor and at least one spring connected to the lever and the frame.

In some preferred embodiments of the present invention rotary tattoo machine having a spring tension adjustment feature, the spring is selected from the group consisting of a leaf spring, a coil spring and a bar spring. In some preferred embodiments of the present invention rotary tattoo machine having a spring tension adjustment feature, the spring is a spring made of a material selected from the group consisting of metal, plastic and combinations thereof.

In some preferred embodiments of the present invention rotary tattoo machine having a spring tension adjustment feature, the spring mechanism includes an attachment component that is connected to and removable from the frame.

In some preferred embodiments of the present invention rotary tattoo machine having a spring tension adjustment feature, the at least one spring is a single spring.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE SEVERAL VIEWS OF THE DRAWINGS(S)

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION OF THE EMBODIMENTS

Figure 1:
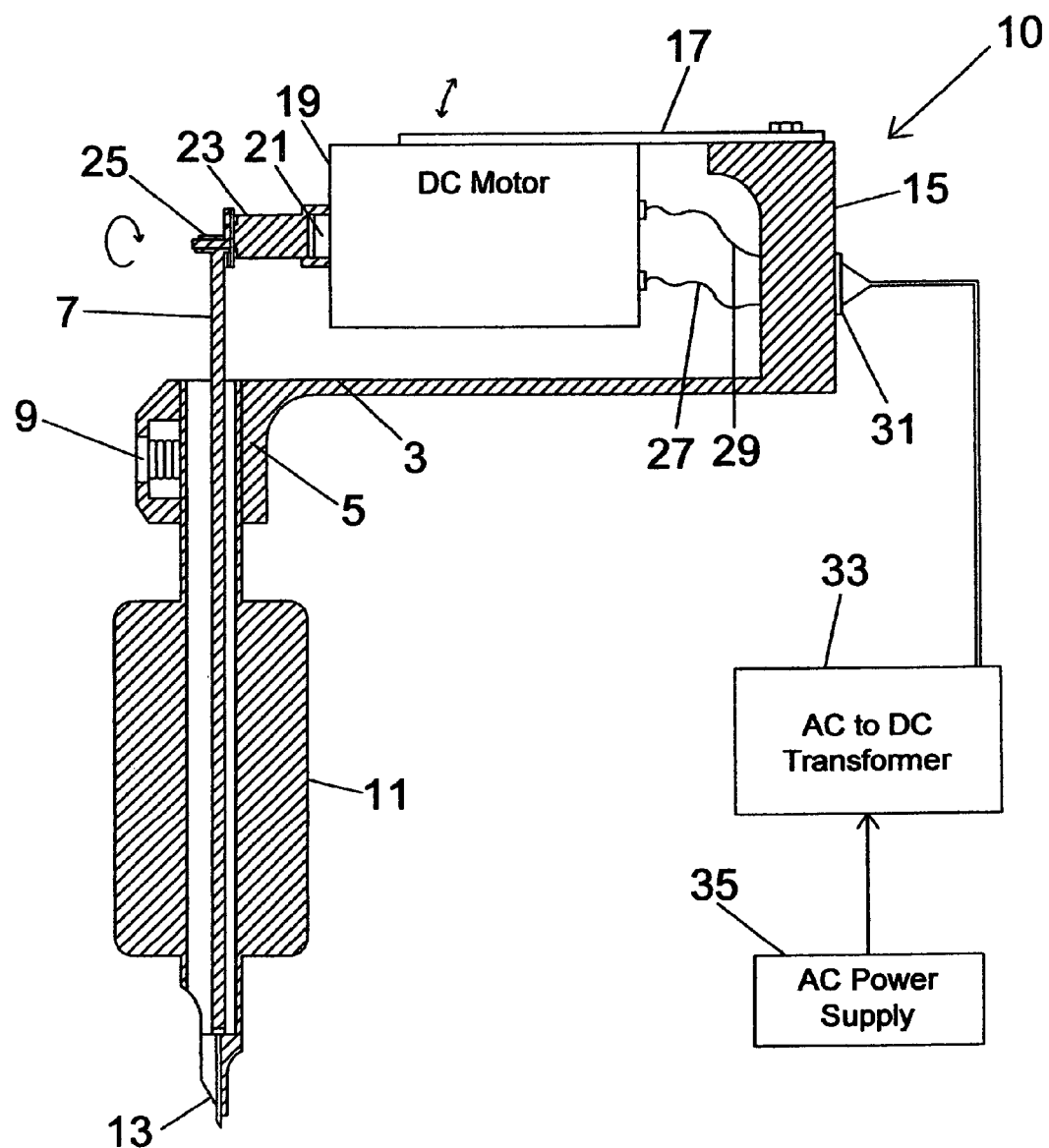
FIG. 1 shows a side cut view of one preferred embodiment of the present invention rotary tattoo machine.

In the professional tattoo industry, tattoo machines have been in use for many years, and have competed and survived over the decades due to inherent advantages and disadvantages of each. A tattoo machine typically has a reciprocating needle that moves up and down within a tubular structure, carrying ink into the skin of an individual in the process. The reciprocating needle typically punctures the skin at a high rate. The needles are installed in the machine and dipped in ink, which is sucked up through the machine's tube system. Then, the tattoo machine induces an up-and-down motion of the needle to puncture the top layer of the skin and drive insoluble particles of ink into the dermal layer of skin.

The two tattoo machines mentioned above are the coil tattoo machine and a rotary tattoo machine. Coil tattoo machines are more widely used currently due to their relative availability and relatively lower cost. A coil tattoo machine employs an electromagnetic circuit to move the needle grouping up and down. Differentiations and variants can be found in a wide array, ranging from single coiled machines to triple coiled machines. Generally, the coil tattoo employs one or more DC coils and spring point(s) that induce the linear up and down motion of a bar that is coupled to the needle. Coil tattoo machines typically allow some "give" in the needle (i.e., absorb some of the force resulting when the needle impacts the skin), inhibiting blowout that is caused when the needle extends too far into or beyond the dermal layer of skin. However, coil tattoo machines are generally relatively heavy and more difficult to maneuver during use. In addition, the electromagnetic switching of coil type tattoo machines generates a significant amount of noise, which can turn off first-time customers who may already be hesitant about getting a tattoo. Further, coil tattoo machines can be used as either a liner or a shader, but not both, since shaders generally have thicker barrels and typically need heavier coils to produce the extra power needed to drive the ink into the skin, while liners typically have thinner barrels and lighter coils for extra comfort.

The conventional rotary tattoo machine uses an electric motor with a rotatable shaft that is coupled with the needle to drive the needle in the reciprocating up and down motion. Rotary tattoo machines can offer several advantages over the coil machines because a rotary tattoo machine is typically lighter weight, substantially less noisy, and can be used as either a liner or a shader. However, the rotary tattoo machines typically do not allow the needle to "give" (i.e., absorb some of the impact force between the needle and the skin) when the machine is pushed too hard against the skin, which can result in blowout when the needle pierces too far into or beyond the dermal layer of skin. Thus, the present invention is directed to the creation of a rotary tattoo machine that offers all of the advantages of both the rotary tattoo machine and the give of the conventional coil tattoo machine. In the present invention, this is achieved by a spring mechanism attached to the D.C. motor of the machine. In some embodiments of the present invention rotary tattoo machine, one or more springs are connected directly to the D.C. motor, whereas in other embodiments, the D.C. motor is indirectly connected to one or more springs.

FIG. 1 shows a side cut view of one preferred embodiment of the present invention rotary tattoo machine 10. Rotary tattoo machine 10 includes a frame 3 that is adapted to hold and support other components and, thus, has a downwardly projecting front section 5 and an upwardly projecting back section 15. Section 5 has an open cylindrical portion for receiving handle with needle tube 11 and a set screw 9 to enable the removal of handle with needle tube 11, for cleaning or replacement. Section 15 performs a number of functions and in conventional tattoo machines rigidly holds the D.C. motor in place. In the present invention, however, section 15 supports bar spring 17 which is fixedly attached to D.C. motor 19 so that D.C. motor 19 and other aspects attached to it has inherent give due to slight flexibility of spring 17. D.C. motor 19 includes rotating shaft 21 and cam shaft 23. Attached to the off center peg of cam 23 is needle drive mechanism 25, connected to needle 7 which extends below distal end 13, as shown. D.C. motor wires 27 and 29 extend through section 15 of frame 3 to a D.C. plug outlet 31. A.C. power supply 35 (such as conventional house current) is connected to transformer 33 for conversion of the A.C. power to D.C. power which is then plugged into D.C. plug outlet 31. (Conventional speed controls or pedals and other conventional aspects, such as handle choices, are not shown). When the power is turned on, D.C. motor 19 drive cam 23 to create reciprocal motion of needle 7 (circular motion at its top). When a professional user applies machine 10 to the body of a tattoo receiver, spring 17 provides the give not otherwise achieved with rotary tattoo machines.

Figure 2:
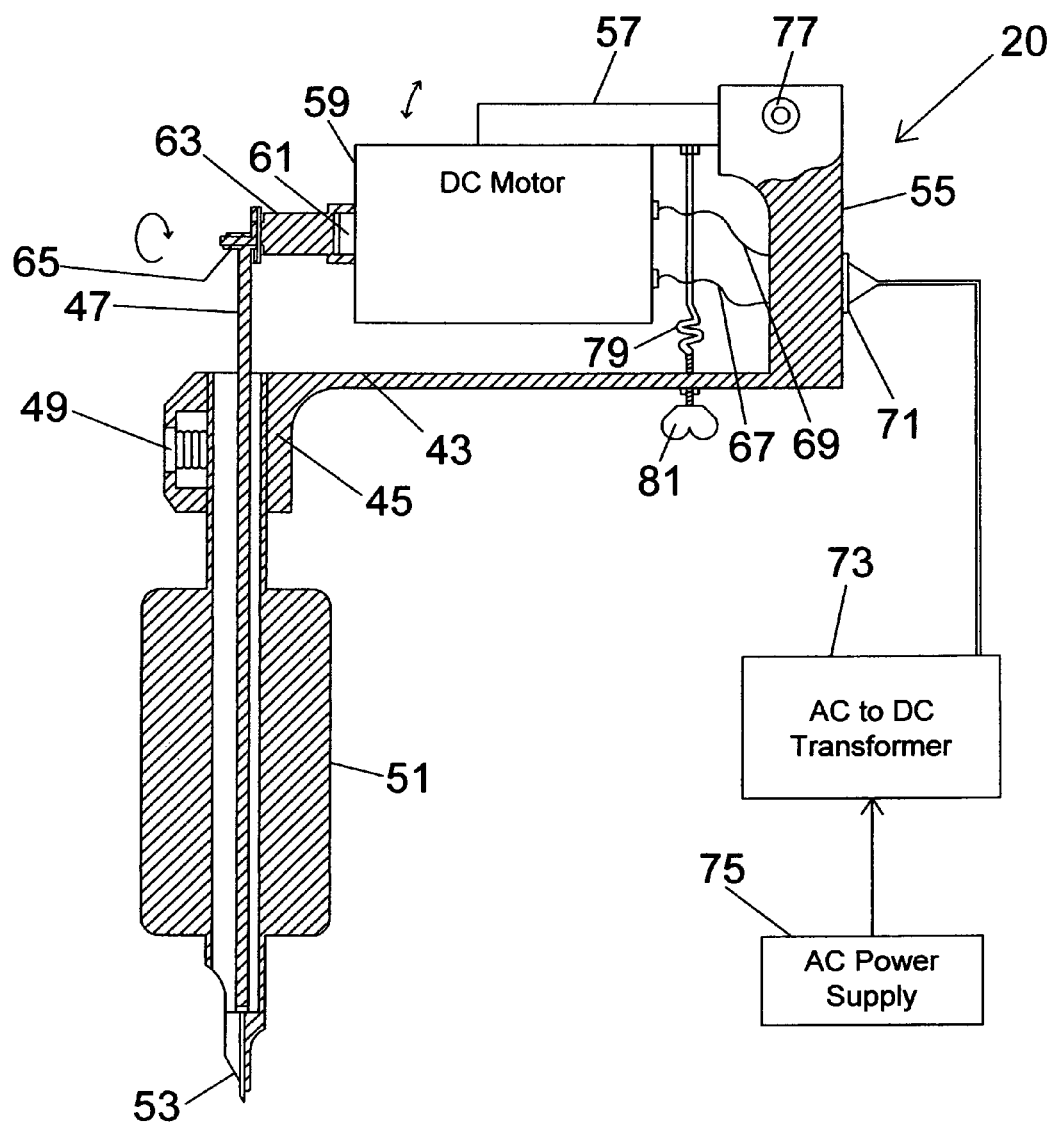
FIG. 2 shows a side cut view of another preferred embodiment of the present invention rotary tattoo machine that includes spring tension adjustment.

FIG. 2 shows a side cut view of another preferred embodiment of the present invention rotary tattoo machine 20 that includes a spring tension adjustment feature. Rotary tattoo machine 20 includes a frame 43 that is adapted to hold and support other components. It has a downwardly projecting front section 45 and an upwardly projecting back section 55. Section 45 has an open cylindrical portion for receiving handle with needle tube 51 and a set screw 49 to enable the removal of handle with needle tube 51, for cleaning or replacement. Section 55 supports lever 57 via axel 77. Lever 57 is thus rotatably connected to section 55 and is fixedly attached to D.C. motor 59. There is an adjustable spring 79 with adjustment key 81 that is attached to lever 57 at its top and to frame 43, as shown. Spring 79 restricts the motion of lever 57 to a small arc and lever 57 then, in turn restricts the movement of D.C. motor 59 to a slight arc. D.C. motor 59 includes rotating shaft 71 and cam shaft 63. Attached to the off center peg of cam 63 is needle drive mechanism 65, connected to needle 47 which extends below distal end 53, as shown. D.C. motor wires 67 and 69 extend through section 55 of frame 43 to a D.C. plug outlet 71. A.C. power supply 75 (such as conventional house current) is connected to transformer 73 for conversion of the A.C. power to D.C.

power which is then plugged into D.C. plug outlet 71. When the power is turned on, D.C. motor 59 drive cam 63 to create reciprocal motion of needle 47 (circular motion at its top) and when a professional user applies machine 20 to the body of a tattoo receiver, spring 79 with lever 57 provides the give not otherwise achieved with rotary tattoo machines.

Figure 3:
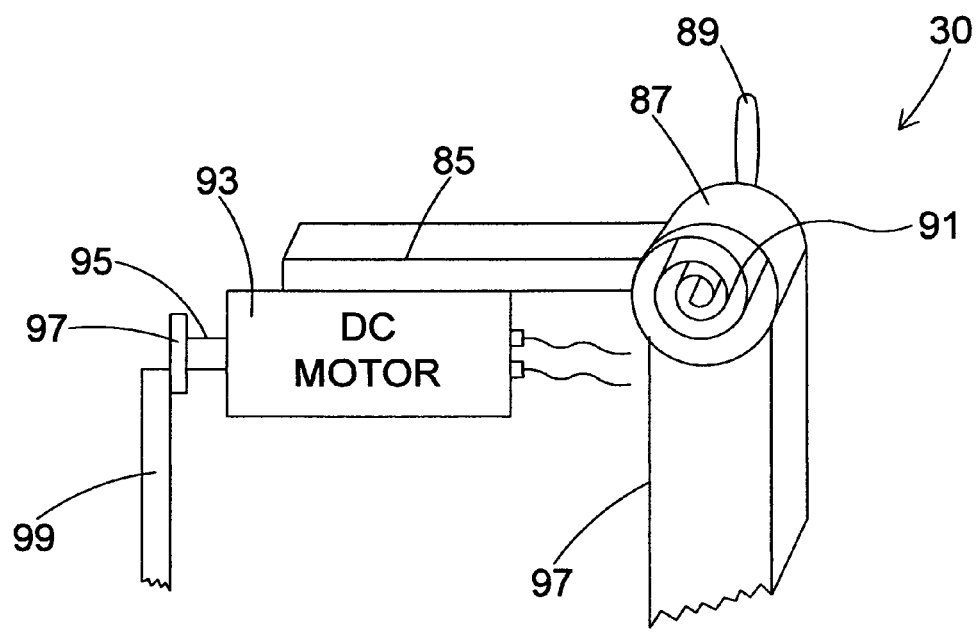
FIG. 3 shows a partial cut view of a third preferred embodiment of the present invention rotary tattoo machine; and, FIG. 4 shows a schematic diagram of important features of the present invention rotary tattoo machine.

FIG. 3 shows a partial cut view of a third preferred embodiment of the present invention rotary tattoo machine 30. It includes frame 97, lever 85, coil spring 87, spring tension adjustment shaft 89 and D.C. motor 93. The motor 93 may be connected to power in any known manner, for example, as shown in FIGS. 1 and 2 above. Motor shaft 95 turns cam 97 and thus moves needle 99. This Figure is shown to illustrate one type of coil spring.

Figure 4:
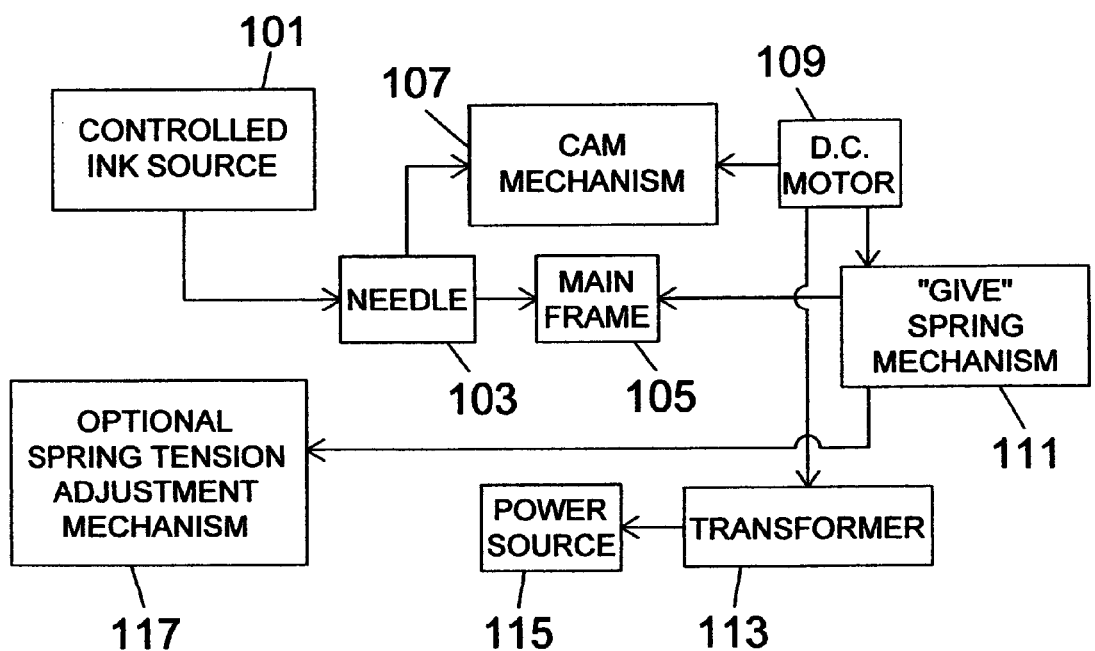

FIG. 4 shows a schematic diagram of important features of the present invention rotary tattoo machine. A controlled ink source 101 is used for the tattoo ink, drawn by needle 103. The needle 103 is attached to the cam mechanism 107, which is driven by D.C. motor 109. The motor 109 is suspended by a spring mechanism 111 that provides flexion and hence "give" to the motor 109 down through needle 103. The D.C. motor 109 is powered via transformer 13, which itself has a power source, such as an A.C. power source. Any spring mechanism may be utilized that will enable the motor to move in a small arc. Optional spring tension adjustment mechanism 117 will allow the tattoo artist to adjust the spring and hence, adjust the give depending upon the task and customer involved in a particular process.

Although particular embodiments of the invention have been described in detail herein with reference to the accompanying drawings, it is to be understood that the invention is not limited to those particular embodiments, and that various changes and modifications may be effected therein by one skilled in the art without departing from the scope or spirit of the invention as defined in the appended claims. While the present invention is illustrated by the above drawings, alterations such as design changes, materials of construction, relative angles, such as the shown 90 degree angle between the handle and the D. C. motor could be greater or smaller than the right angle shown. The spring could be located under the D. C. motor instead of above, or behind or in front of it, without affecting the functional aspects of the invention. The spring adjustment mechanism to tighten or loosen the spring tension may be any available spring adjustment mechanism.

What is claimed is:

1. A rotary tattoo machine with suspended motor give, which comprises:
    a) a frame adapted to receive and support rotary tattoo machine components;
    b) a spring mechanism having at least one spring connected to said frame;
    c) a D.C. rotary drive motor connected to said at least one spring and rotatably suspended from said spring mechanism relative to said frame, said D.C. rotary drive motor having a drive shaft and a cam extending therefrom;
    d) a needle drive mechanism connected to said cam; and,
    e) a tattoo needle connected to said needle drive mechanism.

2. The rotary tattoo machine of claim 1 wherein said D.C. rotary drive motor includes connection for a power unit having a corresponding complementary connection of a transformer with a power source connection.

3. The rotary tattoo machine of claim 2 wherein said machine further includes said transformer connected thereto.

4. The rotary tattoo machine of claim 3 wherein said transformer is a variable power adjustable transformer.

5. The rotary tattoo machine of claim 1 wherein said spring mechanism is at least one spring extending from said frame to said D.C. rotary.

6. The rotary tattoo machine of claim 1 wherein said spring mechanism is a rotatable lever connected to said frame and to said D.C. rotary drive motor and at least one spring connected to said lever and said frame.

7. The rotary tattoo machine of claim 1 wherein said spring is selected from the group consisting of a leaf spring, a coil spring and a bar spring.

8. The rotary tattoo machine of claim 7 wherein said spring is a spring made of a material selected from the group consisting of metal, plastic and combinations thereof.

9. The rotary tattoo machine of claim 1 wherein said spring mechanism includes an attachment component that is connected to and removable from said frame.

10. The rotary tattoo machine of claim 1 wherein said at least one spring is a single spring.

11. A rotary tattoo machine with suspended motor give, which comprises:
    a) a frame adapted to receive and support rotary tattoo machine components;
    b) a spring mechanism having at least one spring connected to said frame;
    c) a spring tension adjustment mechanism connected to said at least one spring;
    d) a D.C. rotary drive motor connected to said at least one spring and rotatably suspended from said spring mechanism relative to said frame, said D.C. rotary drive motor having a drive shaft and a cam extending therefrom;
    e) a needle drive mechanism connected to said cam; and,
    f) a tattoo needle connected to said needle drive mechanism.

12. The rotary tattoo machine of claim 11 wherein said D.C. rotary drive motor includes connection for a power unit having a corresponding complementary connection of a transformer with a power source connection.

13. The rotary tattoo machine of claim 12 wherein said machine further includes said transformer connected thereto.

14. The rotary tattoo machine of claim 13 wherein said transformer is a variable power adjustable transformer.

15. The rotary tattoo machine of claim 11 wherein said spring mechanism is at least one spring extending from said frame to said D.C. rotary.

16. The rotary tattoo machine of claim 11 wherein said spring mechanism is a rotatable lever connected to said frame and to said D.C. rotary drive motor and at least one spring connected to said lever and said frame.

17. The rotary tattoo machine of claim 11 wherein said spring is selected from the group consisting of a leaf spring, a coil spring and a bar spring.

18. The rotary tattoo machine of claim 17 wherein said spring is a spring made of a material selected from the group consisting of metal, plastic and combinations thereof.

19. The rotary tattoo machine of claim 11 wherein said spring mechanism includes an attachment component that is connected to and removable from said frame.

20. The rotary tattoo machine of claim 11 wherein said at least one spring is a single spring.

* * * * *